United States Patent
Snelling et al.

(10) Patent No.: US 6,809,820 B2
(45) Date of Patent: Oct. 26, 2004

(54) SMALL PARTICLE ANALYSIS BY LASER INDUCED INCANDESCENCE

(75) Inventors: David R. Snelling, Almonte (CA);
Gregory J. Smallwood, Orleans (CA);
Omer L. Gulder, Vaughan (CA);
Fengshan Liu, Orleans (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/755,232

(22) Filed: Jan. 13, 2004

(65) Prior Publication Data

US 2004/0141176 A1 Jul. 22, 2004

Related U.S. Application Data

(63) Continuation-in-part of application No. 10/124,597, filed on Apr. 18, 2002.

(51) Int. Cl.[7] .............................................. G01N 21/00
(52) U.S. Cl. ....................... 356/337; 356/338; 356/336; 356/315
(58) Field of Search ................................ 356/335–343, 356/351–317, 320; 250/222.2, 227.11, 554, 342, 349, 574–575

(56) References Cited

U.S. PATENT DOCUMENTS

| | | | | |
|---|---|---|---|---|
| 3,858,851 A | * | 1/1975 | Ogle ........................... | 356/336 |
| 4,641,036 A | * | 2/1987 | Ohno et al. ................. | 250/574 |
| 5,654,797 A | * | 8/1997 | Moreau et al. ............. | 356/336 |
| 5,920,388 A | * | 7/1999 | Sandberg et al. ........... | 356/315 |
| 5,986,277 A | * | 11/1999 | Bourque et al. ............ | 250/554 |
| 6,154,277 A | * | 11/2000 | Snelling et al. ............. | 356/338 |
| 6,181,419 B1 | * | 1/2001 | Snelling et al. ............. | 356/335 |
| 2003/0197863 A1 | | 10/2003 | Snelling et al. | |

FOREIGN PATENT DOCUMENTS

WO    PCT/EP97/00638    *    8/1997
WO    WO 97/30335    8/1997

OTHER PUBLICATIONS

"Soot diagnostics using laser–induced incandescence in flames and exhaust flows" by R. T. Wainner and J. M. Seitzman, published in 1999, by the American Institute of Aeronautics and Astronautics.*
U.S. patent application Ser. No. 10/124,597, Snelling et al.
Wainer et al, "Soot Diagnostics Using Laser–Induced Incandescence in Flames and Exhaust Flows", American Inst. Of Aeronautics and Astronautics, Inc., p 1–12.
Hoffnagle et al, "Design and Performance of a Refractive Optical System that Converts a Gaussian to a Flattop Beam", Applied Optics, Vo. 3, No. 30, Oct. 20, 2000, p. 5488–5499.

* cited by examiner

Primary Examiner—Frank G. Font
Assistant Examiner—Sang H. Nguyen
(74) Attorney, Agent, or Firm—Teitelbaum & MacLean; Neil Teitelbaum; Doug MacLean

(57) ABSTRACT

The method and apparatus of laser-induced incandescence (LII) to analyze characteristics of submicron-sized particles are described. LII is recognized as a good tool for determining the characteristics of small particles in a gas, e.g., volume fraction, particle size, and specific surface area. It uses the fact that the incandescence signal is proportional to the volume of the particles. It also uses the fact that transient cooling is dependent on the specific surface area of the particle, which is related to diameter of the particle. In LII, particles are heated by a pulsed laser light beam to a temperature where incandescence from the particles can be distinguished from ambient light. The temperature of particles and their volume fraction governs the incandescence. The temperature decay rate is proportional to the primary particle size. The invention uses an optical arrangement that ensures a near-uniform laser energy distribution spatial profile. The invention also uses a low fluence laser beam pulse to avoid evaporation of particles. Without significant evaporation and with a uniform energy profile, accurate and precise measurements can be conducted more easily and reliably.

26 Claims, 9 Drawing Sheets

SMALL PARTICLE ANALYSIS BY LASER INDUCED INCANDESCENCE

This application is a continuation-in-part of U.S. patent application Ser. No. 10/124,597 filed Apr. 18, 2002.

FIELD OF INVENTION

The present invention relates to a method and apparatus for analysis of submicron-sized particles, such as soot, over a wide range of particle concentrations with high temporal and spatial resolution in particular, it relates to improvements in the Laser-Induced Incandescence technique (LII for short) for improved measurement accuracy by the use of a laser beam of low fluence and/or a good laser energy profile.

BACKGROUND OF INVENTION

The presence of particulate matter, such as soot particles, in the environment has brought about an increased interest in the development of methods and devices for the determination of particulate concentration and its average sizes. Soot in particular has been the subject of study for measurement. However, all small particles pose an important area of interest and concern, particularly for environmental and health reasons. The emission of soot from engines, power generation facilities, incinerators, or furnaces, for example, represents a loss of useful energy and further is a serious environmental pollutant and a health risk. However, the presence of soot in flames can also have positive effects. For example, the energy transfer from a combustion process is largely facilitated by the radiative heat transfer from soot. Thus, to understand soot formation and develop control strategies for soot emission or formation, measurements of soot concentrations are necessary. Other applications include characterization of metal nanoparticles and ceramic nanoparticles. The characterization can be used for monitoring, regulatory compliance, process control production of value-added nanoparticles, and many other applications. LII is a good diagnostic tool for measurements of particulate as the LII signal is proportional to particle volume fraction and is also related to particle sizes.

Current techniques for measuring diesel particulate concentration include the Bosch Smoke Number and direct mass sampling. In the Bosch Smoke Number method particles are collected on filter paper from a portion of the exhaust stream and the light reflection from the collected sample is measured. This is compared against a calibration chart to determine the mass flow. Since sufficient sample material must be collected over time, this method requires a long period for sample collection and has a poor time and spatial resolution. Thus this method cannot provide diagnostic information about the formation of particles in the combustion cycle. The direct mass sampling method is the official regulatory method of the EPA and measures the mass of soot from a difference of the mass of the soot on a filter and the mass of the filter alone. This method, however, has a limited accuracy, particularly for low emission vehicles. Both methods suffer a loss in accuracy when the source produces lower emissions, and require significantly longer testing for low emission combustors.

The measurement of soot particle concentrations has been greatly improved by the development of LII, which can provide concentration information with high temporal and spatial resolution. Previous techniques could not detect small concentrations and could not provide accurate time resolved information regarding soot formation.

LII exposes a volume of gas containing refractory particles, which are particles capable of absorbing laser light energy with an evaporation temperature sufficiently high to produce measurable incandescence, to a pulsed, focused, high-intensity laser light. The particles absorb laser energy, heating to temperatures far above the surrounding gas. At these elevated temperatures (in a range of 4000–4500 K in the case of soot) the particles incandesce strongly throughout the visible and near infrared region of the spectrum. In the past, the regime in which evaporation was the predominant heat loss mechanism limited the maximum particle temperature. For example, any further increase in laser light energy resulted in an increase in the evaporation rate rather than an increase in particle temperature. In accordance with Planck's radiation law, any material gives off energy in the form of radiation having a spectrum and magnitude influenced by its temperature. The higher the temperature is, the greater the intensity is and the shorter the peak wavelength is. Thus the radiative emission at these elevated temperatures increases in intensity and shifts to blue (shorter) wavelengths, compared with that of the surrounding medium. Thus the LII signal is readily isolated from any natural flame emission. Because of the rapid time scale and good spatial resolution, as well as its large dynamic range, LII is well suited as an optical diagnostic to measure soot volume fraction and the particle sizes in turbulent and time varying combustion devices. What was not appreciated heretofore was that optimum results could be achieved by controlling the maximum temperature to be less than a temperature such that evaporation never becomes the predominant heat loss mechanism for a majority of particles within a sample. Therefore, in accordance with this invention, it has been found that optimum results can be obtained by ensuring that no more than 5% of the total solid volume of the particles to be analyzed should be evaporated. Stated differently, preferably 95% of the total solid volume v; of the particles should not evaporate. In a most preferred embodiment less than 2% and preferably 1% or less of the total solid volume of the particles will be evaporated.

Hence, it is an object of this invention to provide a system wherein at least a majority of particles in a sample are heated such that they incandesce and do not significantly evaporate losing a substantial quantity of their solid volume, thereby cooling by way of conduction to a surrounding gas, or medium, rather than through significant evaporation as occurred in the past.

There is an important distinction that is made between "the invention" and the prior art described heretofore. By way of example, the prior art system above, heated a majority of soot particles in a sample, to elevated temperatures between 4000–4500K. At these elevated temperatures two cooling mechanisms were at play; evaporation, and conduction. It was believed at the time, that an advantage of heating particles to these high temperatures was that they incandesced strongly; another advantage was that the LII signal generated was relatively independent of laser fluence, although for unknown reasons; and it was believed that this was an optimum condition.

In patent application WO 97/30335 in the names of Alfred Leipertz et al., published Aug. 21, 1997, a laser-induced incandescence technique is described for determining a primary particle size. The technique taught by Leipertz includes the measurement of the incandescence at two discrete points in time after the laser light pulse, from which a ratio is generated to calculate the particle size according to a mathematical model. However, this technique has been shown to be prone to inaccuracies. Leipertz et al. sample the two measurements at a point of decay where they assume a linear change. This, however, is unlikely to happen until significant cooling has occurred and most of the signal has passed. Thus the signals measured by Leipertz et al are very weak and are highly influenced by noise. Laser fluence (spatial energy density) over the volume measured is also critical to the subsequent temperature decay. It is critical for accuracy to know the energy density profile over the volume. This factor is assumed without verification by the technique of Leipertz et al. Further error is introduced by the detection method, which uses spectrally broadband detectors to measure the signal. The Leipertz et al technique, as a result of these introduced errors, does not provide a good measurement of particle size.

Attempts to characterize particle size are also disclosed in a paper "Soot diagnostics using laser-induced incandescence in flames and exhaust flows" by R. T. Wainner and J. M. Seitzman, published in 1999, by the American Institute of Aeronautics and Astronautics. This article reviews a method to determine particle size by measuring the peak temperature attained (pyrometry) by LII. However, the study found that the temperature of different-sized particles can be identical and thus temperature measurement at the peak is not sufficient to determine particle size.

The present inventors' earlier U.S. Pat. No. 6,154,277 Nov. 28, 2000 and U.S. Pat. No. 6,181,419 Jan. 30, 2001 describe improvements in the LII technique.

U.S. Pat. No. 6,154,277 is directed to absolute intensity measurements in laser-induced incandescence. The invention relates to a method and an apparatus for the determination of particle volume fractions with LII using absolute light intensity measurements. This requires knowledge of the particle temperature either from a numerical model of particulate heating or experimental observation of the particulate temperature. The sensitivity of the detection system is determined by calibrating an extended source of known radiance and then this sensitivity is used to generate absolute LII signals. Further, by using a known particle temperature a particle volume fraction is calculated. This avoids the need for a calibration in a source of particles with a known particle volume fraction or particle concentration. This results in a calibration independent method and apparatus for measuring particle volume fraction or particle concentrations. A modeling process involves a solution of the differential equations describing the heat/energy transfer of the particle and surrounding gas, including parameters to describe vaporization, heat transfer to the medium, particle heating etc. The solution gives the theoretical particle temperature as a function of time.

U.S. Pat. No. 6,181,419 is directed to determining a primary particle size in laser-induced incandescence. The invention relates to a method and apparatus for applying LII to determine a primary particle size of submicron-sized particles. In addition to volume fraction information, particle size can be determined using LII due to the fact that transient cooling is dependent on the diameter of the particle. The ratio of a prompt and a time-integrated measurement from the same laser pulse has been found to be a function of the particle size. A modeling process is the same as that described in the above referenced U.S. Pat. No. 6,154,277. Thus the technique is able to provide more accurate measurements of particle size and particle volume fraction than previous LII techniques, particularly where time averaging is not possible and size measurements must be obtained from a single laser pulse. Calibration is needed to obtain a quantified volume fraction measurement.

In both of the above referenced U.S. Patents, it is stated in essence: Creating a well defined known laser light fluence (laser light energy per unit area, e.g., Joules/cm$^2$) with minimal variation over the measurement volume is important since the incandescent signal is highly dependent on the laser light energy intensity profile. In the model, energy values for particles other than at the peak light intensity is calculated using a uniform distribution of particles about the optic axis aligned with the Gaussian light intensity profile. The particles not located at the peak receive proportionally less light energy and produce a different incandescence signal, as determined in the calibration, which is added cumulatively to determine a total incandescence signal for a given time step. While a Gaussian light intensity distribution of the fluence or light energy is often used, a "top-hat" or square light intensity profile of the laser fluence having a constant light intensity throughout the laser light sheet would be beneficial. In principle any distribution of intensity can be used provided that its distribution through the measurement volume is measured. However, a more uniform light intensity profile ensures that the particulate temperatures are more uniform throughout the measurement volume. This increases the ease and accuracy of the numerical modeling and ensures that the average particulate temperature obtained from multi-wavelengths particulate measurements is more representative of the particle temperature in the measurement volume.

The said patents describe in detail an arrangement that creates a laser light sheet at the volume of the measurement location having a Gaussian fit profile of energy distribution (or fluence) in substantially one plane only. The profile of laser beam light fluence is flat in two orthogonal planes, the third plane being a Gaussian. Such profile is therefore not a true "top-hat" profile and the numerical modeling is required to compensate the effect of varying fluence. With the true "top-hat" profile (a constant low fluence excitation), the results of the numerical modeling are not required to determine the particle volume fraction.

Furthermore, prior work on LII has focused on moderate to high fluence to heat soot particles up to about 4500 K or above where LII signals reach a peak and the soot particles reach evaporation temperatures. This operating point is attractive in that LII signals are relatively insensitive to laser energy (or more precisely laser fluence). At those temperatures, however, the particles are being at least partially evaporated. At temperatures of 4000 K and above, the heat loss of the particles is dominated by evaporation, whereas conduction to the surrounding gas is dominant at lower temperatures. In this specification, therefore, the evaporation temperatures of a particle is defined as the temperatures at which evaporation replaces conduction as a dominant heat loss mechanism of the particle. For soot, therefore, the evaporation temperatures are in the range from 4000 K to about 4500 K, but particles composed of other materials may have different evaporation temperatures. With high evaporation, the particulate is surrounded by a cloud of superheated vapor, which affects the conduction-cooling rate of the particles and therefore affects the temperature decay rate. This, in turn, adversely affects the measurement of primary particle size because the temperature decay rate is proportional to the specific surface area (surface area per unit volume), which is used to determine the particle size. Furthermore, significant evaporation leads to a change in the total particle volume fraction measured and to the final primary particle size. In addition currently available models are not able to accurately predict the cooling behavior in this evaporation regime.

In accordance with this invention, it has been determined that LII signals do not have to be at or near the peak intensity to be measured and thus a laser light of low fluence may be used for LII measurements. With a high fluence laser light, the LII signals and particle temperatures are rapidly changing during the laser pulse due to rapid heating and evaporation of particles. Without evaporation, however, particles go through a relatively smooth conduction phase and produce an initially slower time constant temperature decay due to conduction cooling to the surrounding gas. With no interference from particle evaporation, the time dependent temperature decay reflects more accurately the particle size.

Furthermore, measurements can be made throughout the analyzing period until LII signals drop to the noise level of detectors. By avoiding significant particle evaporation, the concentration and primary particle size do not change during the measurement period, enhancing the reliability, ease, precision, and accuracy of the LII technique. To measure the temperature of particles, the two-color pyrometry technique is used in that the ratio of LII signals measured at two or more wavelengths indicate the temperature of particles. The temperature is measured at many points in time to generate the time dependent temperature decay characteristics.

SUMMARY OF INVENTION

In one aspect, the present invention relates to an improvement in LII and it uses a laser beam of low fluence at the measurement location to avoid heating the particle to a temperature where evaporation is the dominant heat loss mechanism. The temperature of the particles is measured and time dependent decay of the particle temperature is used to analyze the characteristics of the particles.

In a further aspect, the invention uses the two-color pyrometry technique to measure soot particle temperature as a function of time. In other words, it measures LII signals at two or more wavelengths and derives the temperature of soot particles at many points in time. It analyzes a time dependent decaying of the derived temperature of the particles. The decaying of the temperature is indicative of the characteristics of the particles, particularly the size.

In a yet further specific aspect, as LII signals are sensitive to laser energy distribution (fluence), the present invention employs a relay imaging optical arrangement that produces a very uniform fluence profile (also called "top-hat" profile or distribution) throughout the measurement volume. This results in further improvements in accuracy of the LII technique of the present invention as the effect of varying fluence needs not to be compensated by means of the numerical modeling.

In accordance with another aspect of the invention, a method is disclosed for analyzing submicron-sized particles in a defined volume of gas. The method includes steps of heating one or more particles with a pulsed laser light beam to a temperature high enough for the particles to incandesce but less than an evaporation level of the particles and measuring incandescence from the particles at two or more wavelengths at a plurality of time intervals. The method further includes steps of calculating temperatures of the particles from the measured incandescence at a plurality of time intervals, and analyzing the calculated temperatures to obtain characteristics of the particles.

In accordance with a broad aspect of the invention, there is provided a method of analyzing a plurality of submicron sized particles having a total solid volume $v_i$ within a volume of gas, comprising steps of: (a) heating the plurality of the particles to be analyzed with a laser light beam to a temperature such that a majority the submicron particles measurably incandesce, while ensuring that the temperature is sufficiently low such that no more than 5% of the solid volume $v_i$ is evaporated; (b) measuring incandescence from the particles at one or more wavelengths; and (c) determining a characteristic of the particles in dependence upon the measured incandescence in step (b).

In accordance with yet another specific aspect, based on the experimentally derived temperature of particles using a low fluence laser light of non uniform profile, the invention uses the numerical modeling which involves a solution of a differential equations describing the heat energy transfer (heating and cooling) of particles and surrounding gas, to calculate the absolute LII intensities and then generates the soot volume fraction and particle size.

In accordance with another aspect, the method of the invention includes steps of generating a pulsed laser light beam of energy high enough to heat the particles to incandescence, passing the laser beam through an aperture and forming a relay image of the aperture at a measurement location located within the defined volume of gas. The method further includes steps of measuring incandescence from the particles at the measurement location at two or more wavelengths at a plurality of time intervals, calculating temperatures of the particles from the measured incandescence; and analyzing the calculated temperatures to determine characteristics of the particles.

In accordance with a yet further aspect, the invention is directed to an apparatus for analyzing submicron sized particles in a defined volume of gas by using laser-induced incandescence. The apparatus includes a laser for generating a pulsed laser light beam of a predetermined fluence and an optical arrangement including an aperture in an optical path of the pulsed laser light beam for limiting the transmitted pulse to an area of substantially constant fluence; imaging optics for forming a relay image of the aperture at a measurement location located within the defined volume of gas so that one or more particles in the defined volume of gas incandesce. The apparatus further includes at least one photodetector for measuring incandescence from the particles at two or more wavelengths at a plurality of time intervals, a signal processing unit for calculating temperatures of the particles at a plurality of time intervals and a signal analyzer for analyzing a time dependent decaying of the calculated temperatures to obtain characteristics of the particles.

In accordance with a further aspect, an apparatus of the invention includes a laser for generating a pulsed laser light beam of a predetermined fluence, and an optical arrangement for directing the pulsed laser light beam to heat the particles to a temperature high enough for the particles to incandesce but less than an evaporation level of the particles. The apparatus further includes at least one photodetector for measuring incandescence from the particles at two or more wavelengths at a plurality of intervals, a signal processing unit for calculating temperatures of the particles at a plurality of intervals and a signal analyzer for analyzing a time dependent decaying of the calculated temperatures to obtain characteristics of the particles.

In accordance with a specific aspect of the invention, a sample of particles, for example soot, can be analyzed by ensuring that a substantial majority of the sample of particles reach a temperature that will allow them to measurably incandesce and wherein the temperature of at least 80% and preferably 95% or more of the particles does not exceed 3900 K during the heating and detecting.

It is a significant advantage that the technique can provide more accurate measurements with high temporal and spatial resolution from a single laser light pulse, even for low particle concentrations. This is in part because of the use of more uniform energy distribution or "top-hat" distribution of the laser light, and further to the reduction in errors due to evaporation effects.

A further advantage is that the apparatus in accordance with the present invention adapts the LII technique for in situ application, particularly with the convenience of absolute intensity measurements without the need for an additional calibration setup.

In summary improved accuracy on the volume particle fraction is obtained using the method in accordance with this invention. Simply stated, if a substantial amount of volume of the particles is evaporating during the process of analyzing a characteristic of the particles, optimum analysis is not achieved. In fact, the accuracy of the analysis is inversely related to the amount of solid particle volume loss.

Furthermore, improved accuracy for the measurement of the primary particle diameter is dependent upon the cooling rate of the particles; since the cooling rate of the particles is affected when they cool into an atmosphere of cooling plasma, i.e. evaporating particle gases, this limitation is substantially obviated by ensuring that significant evaporation and hence solid volume loss does not occur.

Additional advantages will be understood to persons of skill in the art from the detailed description of preferred embodiments, by way of example only, with reference to the following figures.

BRIEF DESCRIPTION OF THE DRAWINGS

Like numerals are used throughout the drawings to indicate like elements.

DETAILED DESCRIPTION OF PREFERRED EMBODIMENTS

Within this specification the term measurable incandescence shall have the meaning having an incandescence that can be measured, for example by a photodetector or other detecting element The term solid volume shall mean the physical space occupied by the refractory submicron particles.

The term evaporation with reference to a particle shall mean the loss of solid volume, which is given off as a gas into the surrounding atmosphere.

The incandescent signal is highly dependent on the laser energy profile. Therefore it is advantageous to create known well-defined laser fluence with minimal variation across the measuring volume. Known LII instruments have not been successful in generating a truly uniform laser energy distribution across the measuring volume. As described in the aforementioned earlier patents, a good compromise so far is a square (top hat) profile in two orthogonal planes. The invention provides a good optical arrangement that realizes the laser energy distribution in a substantially uniform profile in three orthogonal planes across the measuring volume, thus improving the accuracy of the LII technique. The present invention uses an optical technique known as relay imaging to produce a highly uniform energy profile.

In addition, conventional LII uses a laser beam of moderate to high fluence to heat soot particles up to temperatures of 4500 K, where the heat loss of the particles is dominated by evaporation. Although the particulate volume fraction may be determined accurately at the peak intensity of the LII signals for moderate laser fluence, this is not so for high laser fluence, where significant evaporation is occurring. In any regime where evaporation dominates, there is a low probability of accurately determining the primary particle size, because the conduction-cooling rate (i.e., the time dependent temperature decay) of the particles, instead of the evaporation, determines the particle size. The conduction-cooling rate in this regime, however, is difficult to predict accurately using currently available models of soot heating and cooling, due to non-equilibrium conditions and unknown gas phase composition and temperature. The invention therefore improves conventional LII techniques by using a low fluence laser beam, thus avoiding temperatures where evaporation is the dominant heat loss mechanism.

Figure 1:
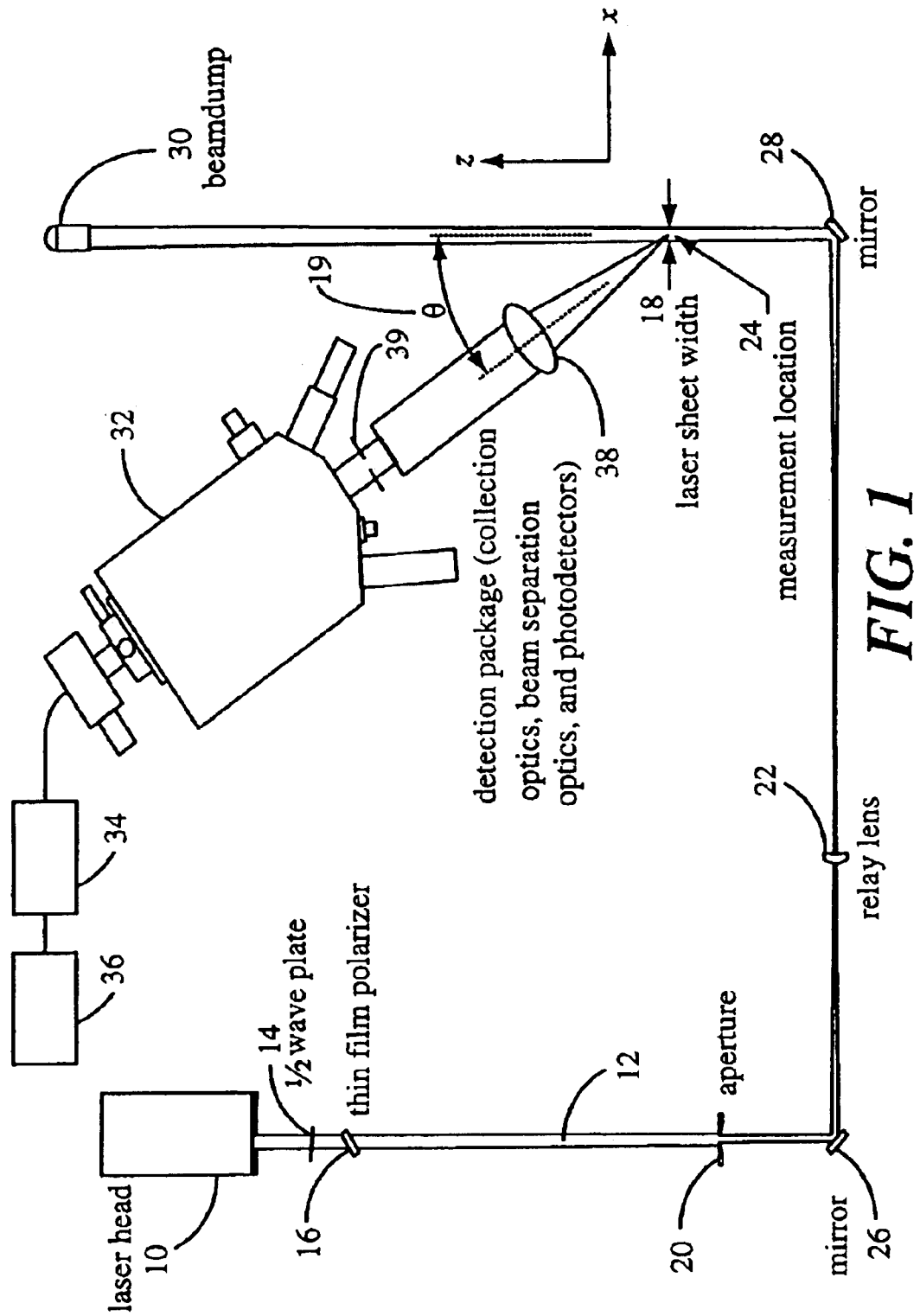
FIG. 1 is a schematic illustration of a preferred embodiment of the apparatus employing an optical arrangement that produces a top hat profile of energy distribution.

One embodiment of an apparatus in accordance with the present invention is illustrated in FIG. 1. A laser 10 directs a pulsed light beam 12 through a half wave plate 14 and thin film polarizer 16 to control the laser energy. The laser beam passing through a rectangular aperture 20 is relay imaged by a relay lens 22 onto a measurement location 24. Specifically, the aperture size is chosen to select the central, constant-fluence part, of the laser beam. The relay lens 22 is selected so that the plane of the aperture 20 is imaged at the measurement location 24 by this lens in order to avoid transmitting diffraction effects from the aperture 20 to the measurement location 24. Mirrors 26 and 28 are used to make the optical arrangement more compact. A beam dump 30 absorbs all the laser energy that passes through the measurement volume. A detection package 32 contains a collection optics for gathering LII light and a beam separation optics that separates LII light to beams of two or more different wavelengths, and separate photodetectors for detecting LII lights of different wavelengths. The collection optics defines the size of the measurement volume. The intersection of the path of laser light beam 12 and the cross-sectional area of the laser beam viewed by the collection optics determine the measurement volume. This region is effectively defined by the image of the circular collection aperture 39 generated by lens 38 at the measurement location 24. The beam separation optics in the detection package 32 uses a lens to collimate the light from the collection aperture 39 and then uses an optical splitter, which spectrally separates this beam into two or more parts. Photodetectors with interference filters in front of them then simultaneously detect the LII signals at two or more different wavelengths. In this embodiment, photodetectors simultaneously but separately detect signal at wavelengths of 780 and 400 nm.

Optionally, the optical splitter can divide the input signal beam into different light wavelength bands. Transient digitizer 34 digitizes analog signals into digital signals for processing at a computer 36. The computer 36 contains digital signal processing units and storage units, the later of which stores necessary software for performing digital signal analyses and if necessary as in other embodiments, numerical modeling, for generating results of experiment, such as, LII absolute intensities, temperatures of soot, an average particle size, and particle concentration.

In a second embodiment of this aspect of the invention, the constant fluence profile is generated by an aspheric lenses, which have been shown to convert beams of known spatial profiles to 'tophat' profiles. This was disclosed in a paper "Design and performance of a refractive optical system that converts a Gaussian to a flattop beam" by J. A. Hoffnagle and C. M. Jefferson, published in 2000, by the Optical Society of America, This approach offers a further advantage in that it does not involve a loss of energy due to the aperture.

A pulsed focused light beam (approximately 10 ns duration) from laser 10 provides an energy source for substantially instantly heating particles contained in the measurement volume 24 and for letting them cool more gradually. Several mJ of energy are sufficient to rapidly heat the particles in the laser beam to their evaporation temperature (approximately 4500 K in the case of "soot"). The present invention, however, uses an energy density (or fluence) to heat particles to a temperature sufficiently high to produce measurable incandescence but not high enough to cause significant evaporation. At such temperatures the particles radiate incandescence as they cool back to ambient temperature by mainly heat conduction to surrounding gas, the ambient temperature typically being 1500–2000 K in combustion systems, and much lower in engine exhausts and ambient environments. The incandescence signals are collected and imaged to a pair of photodetectors at two wavelengths. Digitizer 34 samples incandescence signals simultaneously but separately at a certain interval, e.g., at every 2 ns, and generates corresponding digital signals to send to computer 36 for further processing. Computer 36 processes the intensities of LII signals at two wavelengths to generate the temperature of particles and its time dependent changes. The time dependent temperature changes (decays) are indicative of the average size of the primary particles.

Computer 36 contains software for a numerical modeling, based on parameters of the measuring set-up, such as laser beam geometry properties, gas properties and particle properties. In one of the preferred embodiments thus far described, which measures LII at two wavelengths to obtain experimental soot temperature and uses an essentially constant fluence excitation to ensure that the observed temperature is constant within the measurement volume, the soot volume fraction can be calculated without recourse to the numerical modeling. The ratio of intensities at the two wavelengths provides a temperature and with this temperature and the measured absolute intensities the soot volume fraction can be calculated. If the excitation fluence is not constant throughout the measurement volume then the experimental temperature is an average one, and results of the numerical modeling are used to calculate the soot volume fraction from this average temperature. If intensity is only measured at one wavelength then the soot temperatures and the soot volume fractions have to be derived from the results of the numerical modeling. Computer processes and calculations will be described in detail below.

A suitable laser 10 is a multi-mode laser manufactured by Big Sky Corporation. Other lasers can also be used, such as a pulsed diode laser, a high repetition rate laser or other pulsed lasers, provided that laser energy density sufficient to produce measurable incandescence is delivered to the excitation volume in a sufficiently short time, given the wavelength, beam geometry and particulate composition. The laser pulse duration should be substantially less than the intensity decay rate so that the latter can be measured with sufficient time resolution.

Attenuation of beam 12 is controlled, for example by using a half wave plate 14 to rotate the plane of polarization in combination with a linear polarizer 16 to control the energy delivered to the measurement volume. This method of attenuation is preferred, as the original laser beam spatial and temporal profiles are maintained, and the energy can be continuously attenuated from maximum to minimum. Other methods to reduce the energy in the laser beam could include reducing the flashlamp energy, which would change the laser profile, or inserting neutral density filters, which provide step changes in energy, and may be damaged by the laser beam.

Control of the temperature of the particles, such that a majority of the submicron particles measurably incandesce, while ensuring that no more than 5% of the solid volume $v_i$ is evaporated, is effected, for example, by a suitably programmed computer 36 monitoring the temporal maximum temperature from each laser pulse based on the input signals from the detectors and having means to control the laser energy by actuating a motor to set the angular position of the half wave plate 14. This method of control is preferred, as the optimum temperature can be maintained indefinitely. Other methods of control of the temperature, based on a suitably programmed computer or a skilled operator effecting manual control, include monitoring and controlling the fluence to known levels, monitoring and controlling the laser energy to known levels, or monitoring the particle volume fraction during the laser pulse and the subsequent signal decay period and controlling the laser fluence or energy as required.

According to one of the embodiments, the invention produces an ideal distribution of laser fluence, which is uniform throughout the measurement volume 24. The rectangular aperture 20 is chosen to select the, essentially, constant fluence central region of the laser beam and relay lens 22 then images this essentially constant fluence profile at the measurement volume 24. This ensures that the uniform fluence profile is retained at the measurement volume and that the diffraction effects of the aperture are avoided. The size, geometry, and location within the laser beam of the aperture will determine its effectiveness at maximizing the uniformity of the spatial laser fluence profile. Relay imaging of the aperture minimizes the presence of diffraction from the edges of the aperture at the measurement location. Circular apertures could be employed. However, rectangular or slit apertures are preferred, as the aperture can then be oriented such that the thickness of the laser beam 12 is constant over the region imaged by the detectors. The thickness of the laser beam is defined as the dimension of the beam normal to the laser beam axis, in the plane defined by the intersection of the laser beam axis and the detection optics axis.

Figure 2:
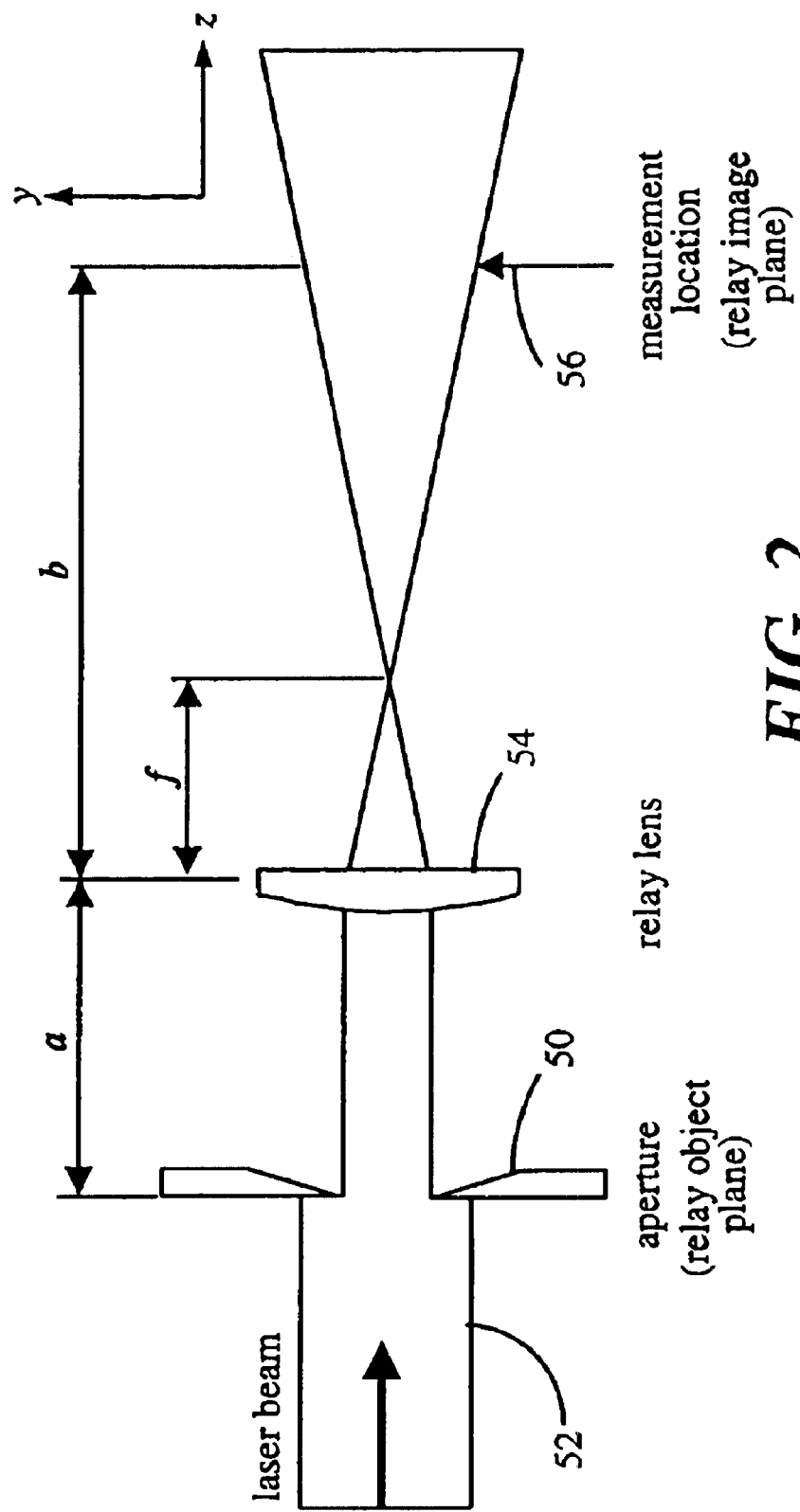
FIG. 2 illustrates a schematic of a single lens relay imaging.

A relay imaging arrangement forms a real image of a beam-defining aperture at a point ("relay image plane") through an optical system. The effective optical propagation distance is reset to zero at this image location, so that an image-relayed system has less beam modulation from diffraction than an unrelayed system. When a coherent light beam is apertured to eliminate part of the laser beam this produces diffraction patterns but relay imaging removes this diffraction pattern at the image plane. FIG. 2 shows schematically a single lens relay imaging arrangement according to one embodiment of the invention. In the Figure, a rectangular aperture 50 which selects the central, essentially constant fluence region, of the laser beam 52 is positioned at a relay object plane and a relay lens 54 images the aperture at a relay image plane 56. The components designated by 50, 52, 54 and 56 in FIG. 2 correspond to components shown in FIG. 1 by numerals 20, 12, 22 and 24 respectively The locations and focal lengths of the one or more relay lenses are chosen so that they simultaneously achieve the desired beam magnification and image the aperture plane at the measurement location. In normal practice, two or more lenses may be required to achieve both the required beam shape and ensure that the aperture plane is imaged by the combination of lenses at the measurement volume. In this embodiment, however, one lens is sufficient to produce a relay image of a rectangular aperture at the measurement volume. The diffraction, which would contribute to the degradation of the desired beam profile, is thus minimized, producing a "top hat", or uniform, fluence distribution at the measurement volume.

The intersection of the path of laser light beam 12 and the cross-sectional area of the laser beam viewed by the collection lens 38 determine the measurement volume. This volume is effectively defined by the image of the circular collection aperture 39 generated by lens 38 at the location of the volume. The measurement volume is typically a cylindrical shape where the circular cross-section is defined by the image of the circular collection aperture 39, and the length of the cylinder is determined by the thickness of the laser sheet 18 and the crossing angle 19, θ, between the laser beam axis and the detection optics axis. It is particularly difficult to characterize the laser fluence when it varies in all spatial directions. Thus by using only a small, essentially constant fluence, section of the laser beam and ensuring that in the direction of the sheet thickness the fluence profile is a "top hat" distribution, a uniform intensity is obtained in all three planes across the axis of viewing of the measurement volume.

Other measurement volume shapes may be used, as appropriate to different applications. Preferred for high spatial resolution is the relatively small cylinder through the laser sheet, described above. A larger cylindrical full plane sheet can be used to collect more signal data, if spatial resolution is not critical. Alternatively, by altering the angle of the collection optics, a line of sight volume along the length of the laser light beam can be sampled. It is not necessary to arrange the collection optics perpendicular to the laser light beam. Laser fluence of 0.2–0.8 J/cm² is typically used to excite soot with 1064 nm radiation. The exact fluence is selected to attain the required soot temperatures. As long as the fluence is the same, the variation in pulse duration of a typical Q-switched Nd:YAG laser (namely 10 to 30 nanoseconds) has little or no effect on the amount of evaporation.

Figure 3:
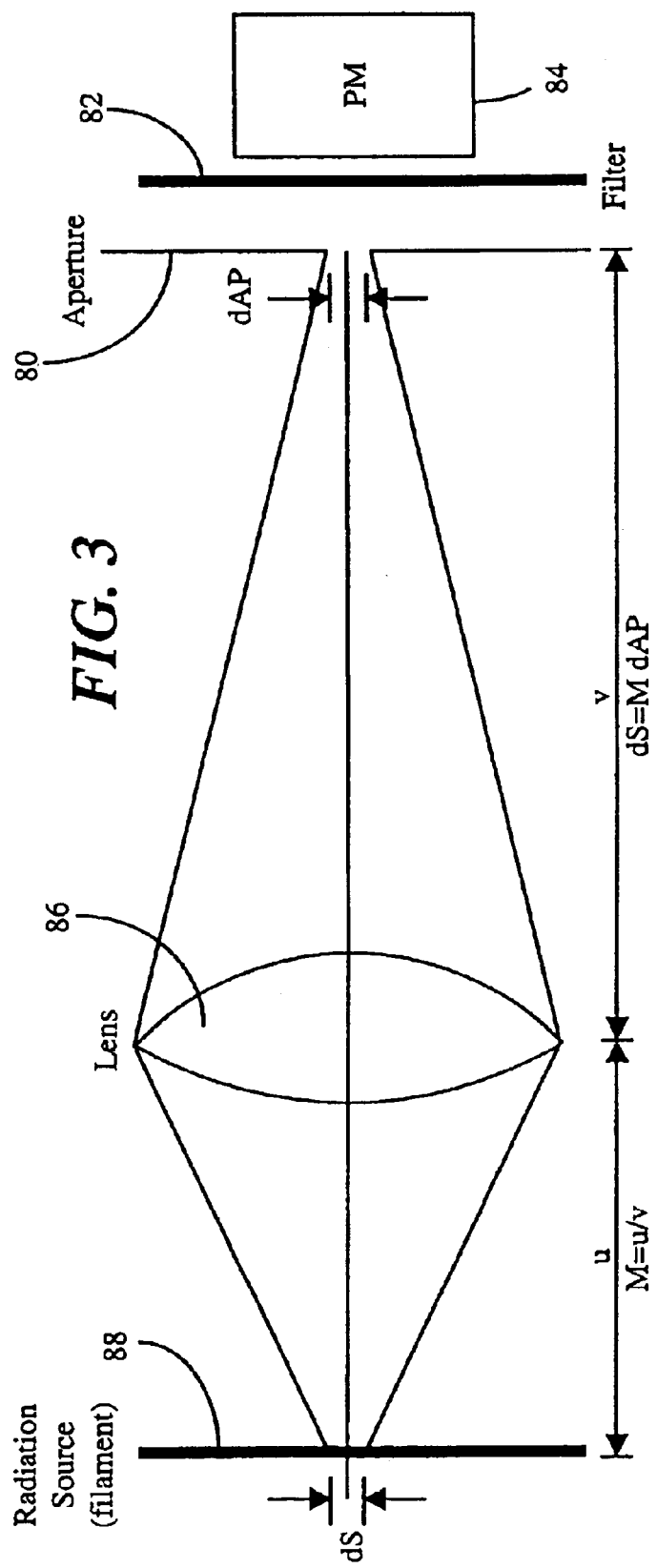
FIG. 3 is an optical schematic for the absolute light intensity calibration using the extended source of known radiance signal.

For obtaining calibration factors $\eta(\lambda_1)$ and $\eta(\lambda_2)$ of the system, an extended source of known radiance (power/unit area of source-steradians-wavelength interval) whose brightness temperature is known is used. In the preferred embodiment a strip filament is used as the extended source of known radiance, the source being larger than the sample cross section. As will be described in detail below, FIG. 3 shows schematically such an arrangement in which lens 86 and an aperture 80 corresponds to lens 38 and aperture 39 shown in FIG. 1. The source light signal is measured by the LII system under calibration to generate an observed signal $V_{CAL}$. A true filament temperature is obtained from the known brightness temperature of the source. A radiance is obtained at a predetermined wavelength from the filament temperature and the known emissivity of the tungsten filament as a function of temperature and wavelength. The spectral radiance of the lamp, i.e. the light power emitted per unit area, per unit solid angle, and per unit wavelength interval and is given by Equation (1):

$$R_S(\lambda, T) = \frac{2c^2 h \varepsilon(\lambda, T)}{\lambda^5} \left[ e^{\frac{hc}{k\lambda T}} - 1 \right]^{-1} \quad (1)$$

wherein $e(\lambda,T)$ is the emissivity of tungsten as a function of wavelength and temperature.

With the known emissivity of tungsten as a function of temperature and wavelength, the filament radiance can be obtained at any desired wavelength from Equation (1).

The radiant power, calibration signal $P_{CAL}$, incident on the detecting system is:

$$P_{CAL} = M^2 A_{AP} \frac{A_L}{u^2} \int_\lambda R_S(\lambda, T_{FIL}) d\lambda \quad (2)$$

where $A_{AP}$ is the area of the lens aperture, $\zeta(\lambda)$ is the filter transmission as a function of light wavelength, $T_{FIL}$ is the filament temperature, $A_l/u^2$ is the solid angle subtended by the lens 86 shown in FIG. 3, and M is the magnification of the detection system. The quantity $M^2 \cdot A_{AP}$ is the cross-sectional area of the filament viewed by the detection system. The integral is over the bandpass of the filter. The observed voltage signal $V_{CAL}$ is:

$$V_{CAL} = GZM^2 A_{AP} \frac{A_L}{u^2} \int_\lambda R_S(\lambda, T_{FIL}) DR(\lambda) \tau(\lambda) d\lambda \quad (3)$$

where DR is the detector response in amp/watt, G is the amplifier gain, and Z is the impedance of the measuring device.

The total (over 4·π steradians) power of light radiated at wavelength λ by a single particle of diameter $d_p$, smaller than the wavelength of light (that is the particle is in the Rayleigh limit), at temperature T is given by Equation (4) below:

$$P_p(\lambda, T) = \frac{8\pi^3 c^2 h}{\lambda^6} \left[ e^{\frac{hc}{k\lambda T}} - 1 \right]^{-1} d_p^3 E(m) \quad (4)$$

In Equation (4), the complex refractive index, m, is m=n+ik where n and k are the real and imaginary parts of the complex refractive index respectively, and the refractive index dependent function, E(m), is $E(m)=\text{Im}\{(m^2-1)/(m^2+2)\}$. Furthermore, c is the speed of light, and h and k are the Planck's and Boltzman's constants respectively.

From Rayleigh-Debye-Gans theory the aggregate emission is, to a very good approximation, the sum of the primary particle emissions that make up the aggregate, which is the number density of these primary particles. In the general case of LII, the soot temperature will be a function of fluence and hence of position in the laser sheet For a "top-hat" fluence profile a single temperature T describes the soot radiation.

The volume of the medium containing the heated particles (soot) imaged onto the detector is closely approximated by a cylinder with a cross-sectional area $M^2 \cdot A_{AP}$ and with a length equal to the thickness of the laser sheet (ignoring any variation in imaged area over the narrow sheet thickness) divided by sin θ, where θ is the angle between the laser beam axis and the detection optics axis. The laser fluence is essentially constant across the end of the cylinder but may have a spatial dependence along the cylinder axis (i.e., through the laser sheet). The experimental LII intensity is then given by:

$$P_{EXP} = \eta_p M^2 A_{AP} \frac{A_L}{4\pi u^2} 8\pi^3 c^2 h d_p^3 \int_\lambda \int_x \frac{\left[e^{\frac{hc}{k\lambda T_p(x)}} - 1\right]^{-1} E(m)}{\lambda^6} d\lambda dx \quad (5)$$

where $n_p$ is the number density of soot primary particles in the viewed volume (assumed constant) and the temperature T is assumed to be a function of x, the position in the laser sheet along the viewing axis. $A_1/4\pi u^2$ is the fraction of this total radiation that is collected by the lens. This is a general form in which constant fluence is assumed in the plane of the laser sheet but not over the remaining spatial variable x. Note that the particle (soot) volume fraction, $f_v$, is $f_v = n_p^3 \pi_p/6$, hence it is not necessary to know the primary particle size in order to calculate the soot volume fraction. The experimentally observed LII signal voltage, $V_{EXP}$ is then given by:

$$V_{EXP} = ZGn_p M^2 A_{AP} \frac{A_L}{4\pi u^2} 8\pi^3 c^2 h d_p^3 \qquad \text{i. (6)}$$
$$\int_\lambda \int_x \frac{\left[e^{\frac{hc}{k\lambda T_p(x)}} - 1\right]^{-1}}{\lambda^6} E(m_\lambda) \tau(\lambda) DR(\lambda) d\lambda dx$$

It is evident from a comparison of Equations (3) and (6) that the magnification, M, the aperture size, $A_{AP}$, and the collection solid angle of the lens, $A_L/u^2$, are common to both equations. Thus the calibration and the expected LII signal depend on the their magnitude in the same way, and the strip filament calibration lamp provides a source of known radiance that can be compared to the particle (soot) radiation, largely independent of any exact knowledge of collection solid angle, or viewing region cross-sectional area. The integration over the filter bandwidth is also common to Equations (3) and (6) and largely cancels, as will be shown in the following section.

The integrals over the filter transmission bandwidth in Equations (3) and (6) are a function of the filter transmission, the signal radiance, and the detector sensitivity since all these quantities can vary with wavelength. However, in practice, to a good approximation, these integrals can be replaced by an equivalent filter with a center wavelength $\lambda_C$, a bandpass $\Delta_\lambda$ and a peak response DRT. If, as above, the detector response is described by DR(λ) multiplied by a constant amplifier gain G then, for a particular detector filter combination an equivalent bandpass can then be defined as:

$$\Delta_\lambda = \frac{\int_\lambda \tau(\lambda) DR(\lambda) d\lambda}{(\tau(\lambda) DR(\lambda))_{max}} = \frac{\int_\lambda \tau(\lambda) DR(\lambda) d\lambda}{DRT} \quad (7)$$

where DRT is the maximuim value attained by the function ζ(λ)·DR(λ) and the integration is over the total filter bandwidth. The center wavelength, $\lambda_C$, is the wavelength limit for which the integral in Equation (7) is ½ of the total integral over all wavelengths. The filter transmission is from $\lambda_C - \Delta_\lambda/2$ to $\lambda_C + \Delta_\lambda/2$.

The integration in, for example, Equation (3) can now be replaced by DRT·$\Delta_\lambda$·R($\lambda_C$), where the lamp radiance at $\lambda_C$, the center of the filter bandwidth is used. Similar expressions can be used for other integrals where R($\lambda_C$) is replaced by the appropriate center line property.

The error involved in the equivalent filter approximation (EFA) of Equation (7) is assessed by comparing it to the results of the full integral expression:

$$R_S(\lambda_C, T_S) DRT \Delta_\lambda = \int_\lambda R_S(\lambda_C, T_S) DR(\lambda) \tau(\lambda) d\lambda \quad (7a)$$

where $R_S(\lambda, T_S)$ can be the radiance of the filament or the soot particle at temperature $T_S$. The error associated with replacing the integral by the radiance at filter center multiplied by an equivalent width, $\Delta_\lambda$ is a function of wavelength, source temperature, detector, and filter bandpass. The error increases as the wavelength and source temperature decrease and increases as the filter bandwidth increases. As an example one of the largest errors encountered (10% error) is for a wavelength of 405 nm, a filter bandwidth of 32 nm, a photomultiplier with a bi-alkali photocathode, and a filament temperature of 1500 K. As the temperature of the source increases the error decreases monotonically and is less than 2% at 2500 K.

If the errors become larger for other combinations of filters and detectors it is straightforward to calculate a correction factor as a function of source temperature to the approximate expression, which can then be applied to the experimental data. As an example, the lamp calibrations can be corrected using a correction factor calculated in this way as a function of lamp current. The calibration was always performed at 3 or more lamp currents and the agreement between these calibrations was an indication that the resulting errors were negligible.

Using the equivalent filter approximation (EFA) Equation (3) becomes:

$$V_{CAL} = GZM^2 A_{AP} \frac{A_L}{u^2} R_S(\lambda_C, T_{FIL}) DRT \Delta_\lambda \quad (3a)$$

Equation (3a) can be rearranged to define a calibration factor η:

$$\eta = \frac{V_{CAL}}{R_S(\lambda_C, T_{FIL})} = GZM^2 A_{AF} \frac{A_L}{u^2} DRT \Delta_\lambda \quad (3b)$$

Using this expression for the calibration factor and using the EFA approximation the expected LII signal, $V_{EXP}$, in Equation (6) can now be expressed as:

$$\frac{V_{EXP}}{\eta} = n_p \frac{2\pi^2 c^2 h}{\lambda_C^6} d_p^3 E(m_{\lambda_C}) \int_x \left[e^{\frac{hc}{k\lambda_C T_p(x)}} - 1\right]^{-1} dx \quad (6a)$$

If the laser fluence is constant throughout the sampled region then the soot is excited to a constant temperature $T_p$ and Equation (6a) can be rewritten as:

$$\frac{V_{EXP}}{\eta} = n_p \frac{2\pi^2 c^2 h}{\lambda_C^6} d_p^3 E(m_{\lambda_C}) \frac{w_b}{\sin(\theta)} \left[e^{\frac{hc}{k\lambda_C T_p}} - 1\right]^{-1} \quad (6b)$$

where the integral over x is replaced as the width of the sheet formed by the laser beam, $w_b$, divided by sin(θ)

where θ is the angle 19 between the laser excitation axis and the viewing axis.

Using Equation (6b) the ratio of the power at two wavelengths, $\lambda_1$ and $\lambda_2$, is given by Equation (8):

$$\frac{P_p(\lambda_1)}{P_p(\lambda_2)} = \frac{\lambda_2^6 \left[ e^{\frac{hc}{k\lambda_2 T_p}} - 1 \right] E(m_{\lambda_1})}{\lambda_1^6 \left[ e^{\frac{hc}{k\lambda_1 T_p}} - 1 \right] E(m_{\lambda_2})} \quad (8)$$

Using the Wien approximation ($\exp(h \cdot c/k \cdot \lambda_C \cdot T_p) \gg 1$) then the ratio of the power at two wavelengths, $\lambda_1$ and $\lambda_2$, given by Equation (8) can be written as:

$$\frac{P_p(\lambda_1)}{P_p(\lambda_2)} = \frac{\lambda_2^6 E(m_{\lambda_1})}{\lambda_1^6 E(m_{\lambda_1})} \exp\left[\frac{-hc}{kT_p}\left(\frac{1}{\lambda_1} - \frac{1}{\lambda_2}\right)\right] \quad (8a)$$

This form of the equation is very convenient for obtaining temperature. The error involved in adopting the Wien approximation increases with increasing temperature and wavelength. As an example the Wien approximation underpredicts the radiation intensity by 1.7% for $T_p$=4500 K and λ=780 nm. The error is smaller for lower temperatures and wavelengths and is negligible for all conditions normally encountered in LII. The error in the Wien approximation can be corrected for, if necessary, by using Equation (8) rather than (8a)

Using Equations (5) and (6) the ratio of powers at wavelengths $\lambda_1$ and $\lambda_2$ can be expressed as:

$$\frac{P_{EXP}(\lambda_1)}{P_{EXP}(\lambda_2)} = \frac{V_{EXP}(\lambda_1)\eta(\lambda_2)}{V_{EXP}(\lambda_2)\eta(\lambda_1)} \quad (9)$$

where the calibration factors are obtained by using the extended sources of known radiance signal at these wavelengths, as is described above. Equation (9) shows how the ratio of the observed signals relates to the ratio of powers at two wavelengths. Equation (8a) can be rewritten as below:

$$\frac{V_{EXP}(\lambda_1)}{V_{EXP}(\lambda_2)} = \frac{\lambda_2^6 E(m_{\lambda_1})\eta(\lambda_1)}{\lambda_1^6 E(m_{\lambda_2})\eta(\lambda_2)} \exp\left[\frac{-hc}{kT_p}\left(\frac{1}{\lambda_1} - \frac{1}{\lambda_2}\right)\right] \quad (10)$$

Using the above observed signal ratio, $V_{EXP}(\lambda_1)/V_{EXP}(\lambda_2)$, the calibration factors and the known values of $E(m_{\lambda,1})$ and $E(m_{\lambda,2})$, Equation (10) can be solved for $T_p$ (temperature). As seen in above discussion, it is only the variation of the particle absorption cross-section with wavelength that is important in determining particle surface temperature. With ideal "top-hat" excitation this temperature represents the actual soot temperature in the sampled volume. However, this temperature, derived from a power ratio measurement at two wavelengths, represents some average particle surface temperature when, for example, a Gaussian fluence profile through the sheet.

Using Equation (6b), the expression for soot volume fraction, $f_v = \pi \cdot d_p^3 n_p/6$, becomes:

$$f_v = \frac{V_{EXP}}{\eta \frac{w_b}{\sin(\theta)} \frac{12\pi c^2 h}{\lambda_C^6} E(m_{\lambda_C})\left[e^{\frac{hc}{k\lambda_C T_p}} - 1\right]^{-1}} \quad (11)$$

With this form of the equation the soot volume fraction can be calculated from experimental measurements and calibration without recourse to the numerical modeling.

The analysis so far assumes that a "top-hat" fluence profile is used to excite the LII, and the soot temperature $T_p$ is constant across the laser sheet. For the more general case where the fluence varies across the laser sheet then Equation (11) must be replaced by:

$$f_v = \frac{V_{EXP}}{\eta \frac{12\pi c^2 h}{\lambda_C^6} E(m_{\lambda_C}) \int_x \left[e^{\frac{hc}{k\lambda_C T_p(x)}} - 1\right]^{-1} dx} \quad (12)$$

Experimentally, some average temperature $T_{av}$ is measured. The average temperature $T_{av}$ is the result of averaging emissions resulting from regions of different fluence. If an effective sheet width is defined as $w_e$, then Equation (12) can be written as:

$$f_v = \frac{V_{EXP}}{\eta \frac{w_e}{\sin(\theta)} \frac{12\pi c^2 h}{\lambda_C^6} E(m_{\lambda_C})\left[e^{\frac{hc}{k\lambda_C T_{av}}} - 1\right]^{-1}} \quad (13)$$

It is not possible to solve this more general case with experimental results alone. When, for example, a Gaussian fluence profile is used, the effective sheet width can only be calculated by resorting to the numerical modeling to be described below.

The numerical modeling is used to calculate the LII radiation as a function of fluence. The integration in Equation (12), across the dimension, x, can then be performed numerically and the integrated radiation intensities can then be used to calculate $T_{av}$ in the same manner as it is done experimentally. The effective sheet width, $w_e$, in Equation (13) can then be calculated from the expression:

$$E(m_{\lambda_C}) \frac{12\pi c^2 h}{\lambda_C^6} \int_x \left[e^{\frac{hc}{k\lambda_C T_p(x)}} - 1\right]^{-1} dx = \quad (14)$$

$$\frac{w_e}{\sin(\theta)} E(m_{\lambda_C}) \frac{12\pi c^2 h}{\lambda_C^6} \left[e^{\frac{hc}{k\lambda_C T_{av}}} - 1\right]^{-1} \quad \text{or:}$$

$$w_e \left[e^{\frac{hc}{k\lambda_C T_{av}}} - 1\right]^{-1} = \int_x \left[e^{\frac{hc}{k\lambda_C T_p(x)}} - 1\right]^{-1} dx \quad (14a)$$

where $T_{av}$ is a temperature derived from the calculated intensity ratios at the two experimental wavelengths, $\lambda_1$ and $\lambda_2$ from:

$$\frac{\lambda_2^6 E(m_{\lambda_1})}{\lambda_1^6 E(m_{\lambda_1})} \frac{\int_x \left[e^{\frac{hc}{k\lambda_1 T_p(x)}} - 1\right]^{-1} dx}{\int_x \left[e^{\frac{hc}{k\lambda_2 T_p(x)}} - 1\right]^{-1} dx} = \frac{\lambda_2^6 E(m_{\lambda_1})}{\lambda_1^6 E(m_{\lambda_2})} \exp\left[\frac{hc}{kT_{av}}\left(\frac{1}{\lambda_1} - \frac{1}{\lambda_2}\right)\right] \quad (15)$$

If only one wavelength is measured experimentally then the model also has to be used to obtain the expected temperatures as a function of time. The temperature $T_{av}$ derived from Equation (15) can now be used in Equation (14a) to calculate $w_e$.

Using the experimentally derived temperature $T_p$ derived from Equation (10) and the theoretically derived equivalent sheet width $w_e$, the soot volume fraction can be obtained from equation (16):

$$f_v = \frac{V_{EXP}}{\eta \frac{w_b}{\sin(\theta)} \frac{12\pi c^2 h}{\lambda_C^6} E(m_{\lambda_C}) \left[ e^{\frac{hc}{k\lambda_C T_p}} - 1 \right]^{-1}} \quad (16)$$

The optical schematic for the absolute light intensity calibration of the extended source of known radiance signal is shown in FIG. 3. In an embodiment of the invention an aperture 80 having a diameter of 1.04 mm is placed in front of a filter 82 and a photomultiplier (PM) 84. This aperture 80 is imaged with a lens 86 onto a radiation source 88. In an embodiment of the invention the radiation source 88 is a strip filament lamp and the aperture 80 is imaged onto the filament of a calibrated strip filament lamp but other extended sources of known spectral radiance, e.g., a blackbody calibration source, can be used for this purpose. Furthermore, in an embodiment of the invention the lens has a focal length of 190 mm, a diameter of 54 mm, and a magnification of M=0.5. The magnification of the lens is determined from the distance u, i.e., the distance between the filament and the lens, and the distance v, i.e., the distance between the lens and the aperture, and equals M=u/v. The calibrated lamp is placed so that its filament is coincident with an LII signal generation region. The lamp, whose filament is 2×8 nm in an embodiment of the invention, has a known brightness temperature at a known wavelength, $\lambda$=649 nm in an embodiment of the invention, as a function of lamp current.

In an alternate embodiment of the invention the radiation source is a quartz halogen lamp, which is calibrated as an irradiance source. In this case, a Lambertian surface is placed at the probe volume, and the quartz halogen lamp is located a precise distance from the surface, corresponding to its irradiance calibration, such that the light intensity scattered from the surface is known, and the calibration factor can be derived from the measured detector signal and the calibrated irradiance."

Once these calibration factors are known, the measured signal can then be converted to an absolute value. Errors associated with uncertainties in the filter characteristics, lens collection efficiency, aperture size, and optical system magnification are shown to be largely eliminated using these calibration procedures. Advantageously, the use of the same optical components for calibration and signal measurement from particles eliminates potential errors. Once a calibration factor is determined, the device can be used, for example in situ, without further calibration.

The particle temperature has now been determined. For a "top-hat" laser fluence profile Equation (11) can now be used to calculate soot volume fraction $f_v$. It is clear from Equation (11) above, that $f_v$ can now be obtained since all other quantities are known.

The time dependent temperature decay is analyzed to determine the specific surface area and the primary particle size. The numerical modeling is also used to generate a theoretical time dependent temperature decay for particles under analysis. The best fit is obtained between the theoretical and experimental temperature decays to derive the average size of the primary particles. The model is optimized for soot particles, but is generally applicable to any particle which absorbs sufficient laser light energy to produce measurable incandescence, and may be applied to other particles such as alumina, silica, and titania and many other metals and metal oxides. The model of this embodiment considers soot aggregates to be made up of uniform, non-overlapping primary spherical particles, although isolated primary particles and aggregates of different characteristics can be modeled similarly with appropriate modifications. The aggregate volume is then found by multiplying the volume of a single primary particle by the number of primary particles within the aggregate, $n_p$.

Figure 4:
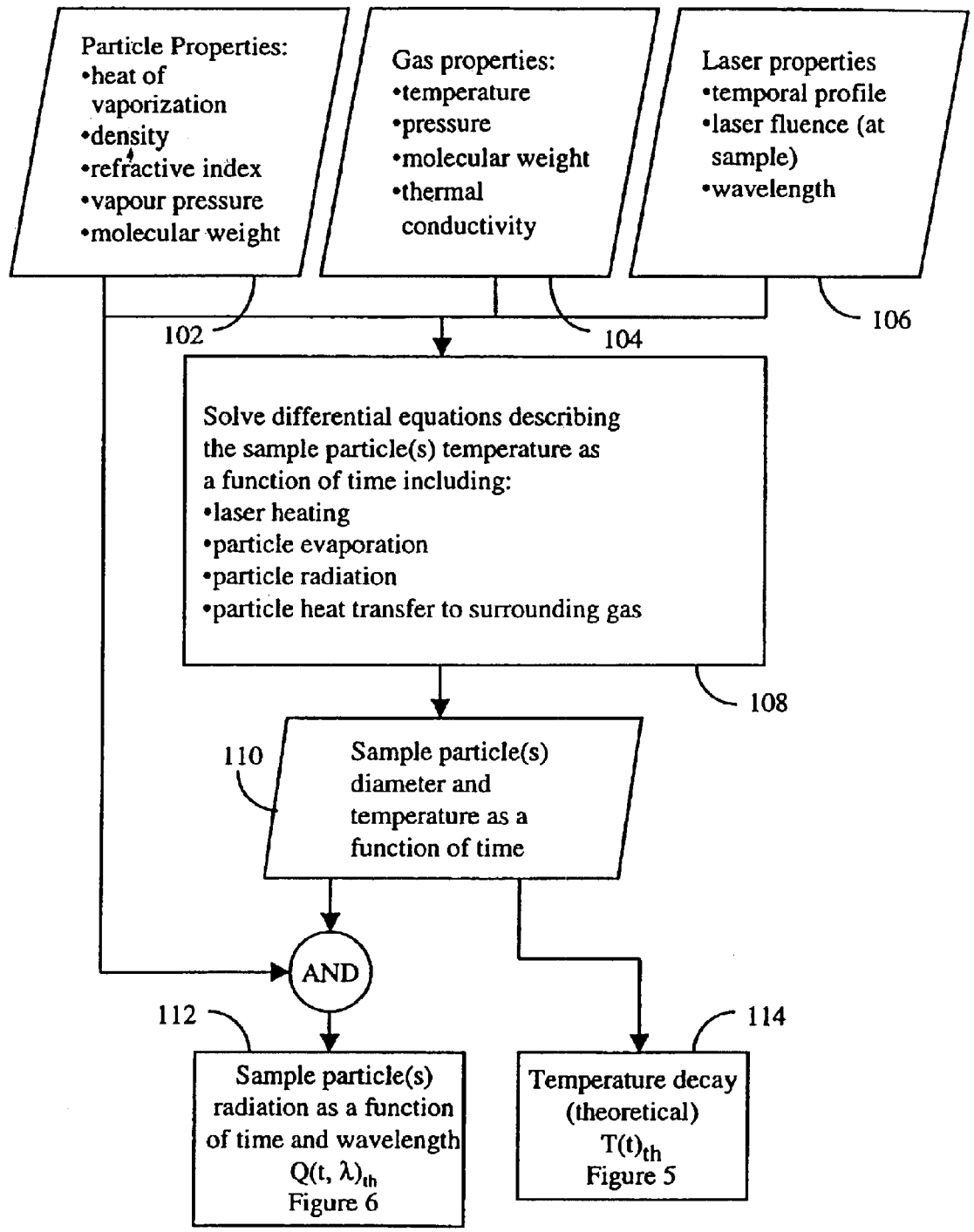
FIG. 4 is a flowchart illustrating the mathematical model process.

A flowchart of the numerical modeling is shown in FIG. 4. First the physical properties of the particle, the gas and the laser are considered as outlined in blocks 102, 104 and 106 respectively. Particle properties 102 include heat of vaporization; density; refractive index; vapor pressure; and molecular weight. Gas properties 104 include temperature; pressure; molecular weight; and thermal conductivity. The laser properties 106 include temporal profile; laser fluence spatial profile at sample; and wavelength. These properties are incorporated to solve the differential Equation (17) below describing the sample particle temperature and diameter as a function of time outlined in block 108.

The heat transfer energy balance equation is Equation (17) below:

$$C_a q - \frac{2k_a(T - T_0)\pi D^2}{(D + G\lambda_{MFP})} + \frac{\Delta H_V}{M_V} \frac{dM}{dt} + q_{rad} - \frac{1}{6}\pi D^3 \rho_2 C_3 \frac{dT}{dt} = 0 \quad (17)$$

Equation (17) includes the absorbed laser light energy, for soot assuming that the particles are aggregates of non-overlapping spheres made up of primary particles and that primary particles are in the Rayleigh limit Equation (17) further includes heat transfer to the surrounding gas, the evaporation of the material, the net particle radiation to the surroundings, and finally the particle heating.

A glossary of terms for Equation (17) follows:
  $\alpha$ $C_a$ particle optical absorption cross section
  $\alpha$ $C_s$ specific heat of particle
  $\alpha$ D primary particle diameter
  $\alpha$ G geometry dependent heat transfer factor $G=8f/(\alpha(\gamma+1))$
  $\alpha$ f Eucken factor (5/2 for monatomic species)
  $\alpha$ accommodation coefficient
    $\gamma$ absorption coefficient of primary particle(=1.4 for air)
  $\alpha \Delta H_v$ heat of vaporization of particle
  $\alpha$ $k_a$ thermal conductivity of ambient gas
  $\alpha$ $M_V$ molecular weight particle vapor
  $\alpha$ M molecular mass of particle
  $\alpha$ q laser intensity
  $\alpha$ T particle surface temperature
  $\alpha$ $T_0$ ambient gas temperature
  $\alpha$ $\lambda_{MFP}$ the mean free path
    $\gamma \lambda_{MFP}=1/(2^{0.5} \times (\sigma_{AB})^2)$ in rigid sphere approximation
  $\rho_s$ density of particle Equation (17) enables the determination of the sample particle diameter in relation to temperature as a function of time indicated in block 110. The experimental and numerical values of particle temperature are combined to generate particle radiation in block 112. A temperature decay in time, on the other hand, is generated in block 114. The temperature decay in time in block 114 is used as the theoretical temperature decay of the particles and is used in the process shown in FIG. 5 to compare with the experimental values, thus determining the particle size. The particle radiation in block 112 is used in the process shown in FIG. 6.

As have been discussed earlier, according to the invention, the particle temperature is measured at a plurality of intervals during a measurement period. A time dependent temperature decay is therefore a measure of the specific surface area and the particle size. By using the above modeling, the particle diameter can be calculated by analyzing the time dependent temperature decay.

Generally speaking, creating a known well-defined laser fluence with minimal variation through the region of the laser beam viewed by the receiver is extremely important since the incandescent signal is highly dependent on the laser energy density (fluence). The particles not located at the peak will receive proportionately less energy, and will produce a different signal as characterized by the spatial profile, which is added cumulatively to determine a total signal for a given time step. The cumulative signal, which simulates the experimentally observed signal, is then used to calculate a simulated temperature using the ratio of the cumulative signal at the two or more experimental wavelengths. In prior LII technologies, a Gaussian profile is commonly used to characterize the laser fluence over the cross section of the laser beam, but with the numerical modeling, any profile can be used as long as it is characterized. Numerical simulations indicate that a laser fluence profile that approaches "top hat" will result in vanishingly small errors.

Figure 5:
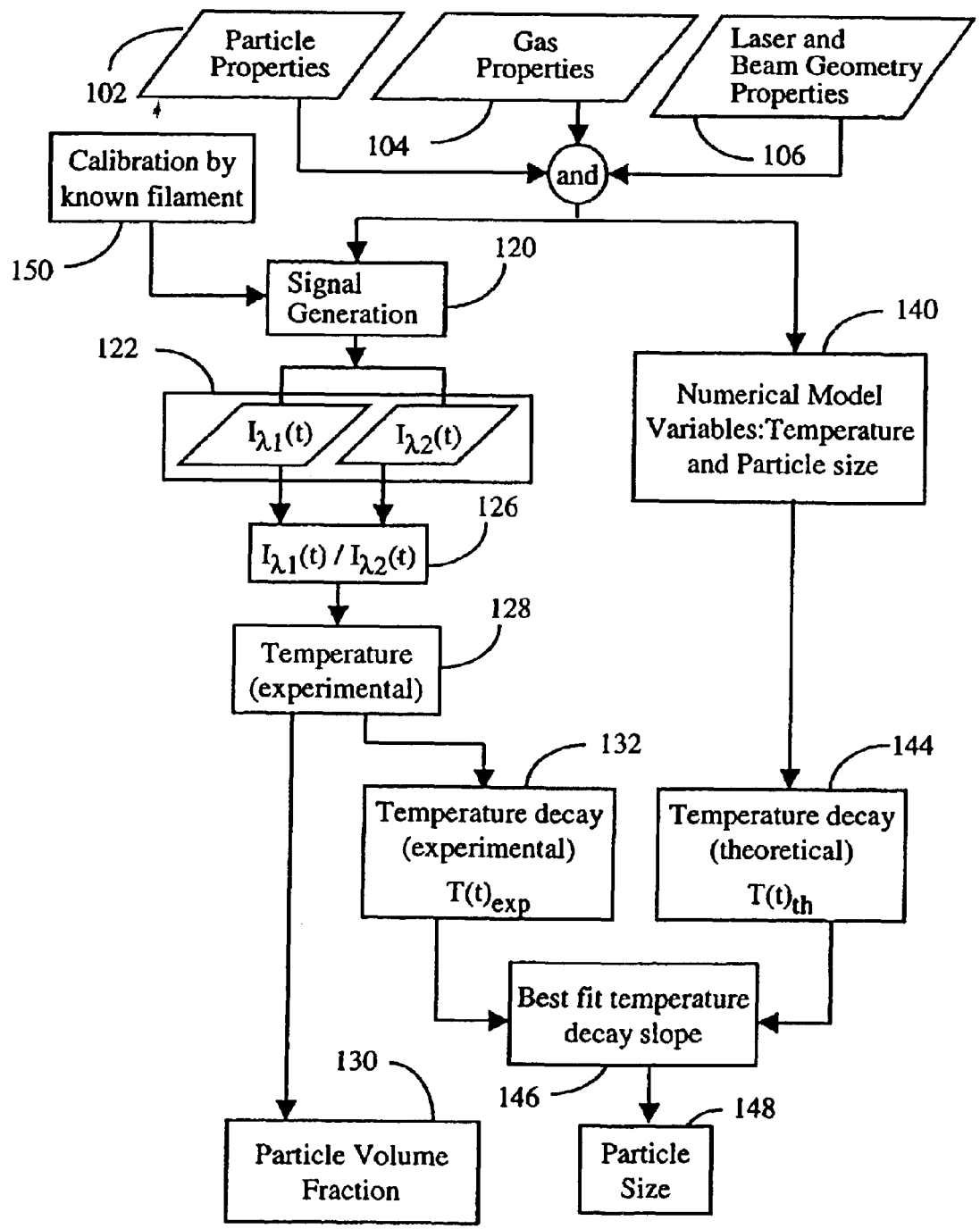
FIG. 5 is a flowchart illustrating the process of the invention according to one embodiment. The process is for determining particle volume fraction and particle size according to the arrangement in which a low fluence pulsed laser light beam and a top hat fluence profile is used.

FIG. 5 is a flowchart outlining the process using a low fluence laser and "top hat" fluence profile, in accordance with one embodiment of the invention. As described thus far, the atop hat" fluence profile ensures that the particle temperature across the measurement volume is constant, thus enabling an accurate measurement of the particle volume fraction. Furthermore, the low fluence pulsed laser light beam ensures that the particle temperature decays in time more smoothly and predictably, thus enabling an accurate measurement of the particle size. Referring to FIG. 5, the particle 102, the gas 104 and the laser beam 106 contribute to the signal generation 120, as discussed in connection with FIG. 4. In this embodiment, the signal generation 120 includes measurements 122 of LII intensity at two or more wavelengths (in this embodiment there are two wavelengths e.g., 780 and 400 nm). The ratio 126 of the LII measurements generates experimental temperature 128, which produces particle volume fraction at 130. Meanwhile, the numerical model 140 is used to generate the theoretical temperature and its time dependent temperature decay curve 144. The experimental 132 and theoretical 144 temperature decay curves are analyzed by best fitting at 146 to produce the average size of particles at 148. Calibration 150 by a known light source can be performed to calibrate LII signals generated at the signal generation 120.

Figure 6:
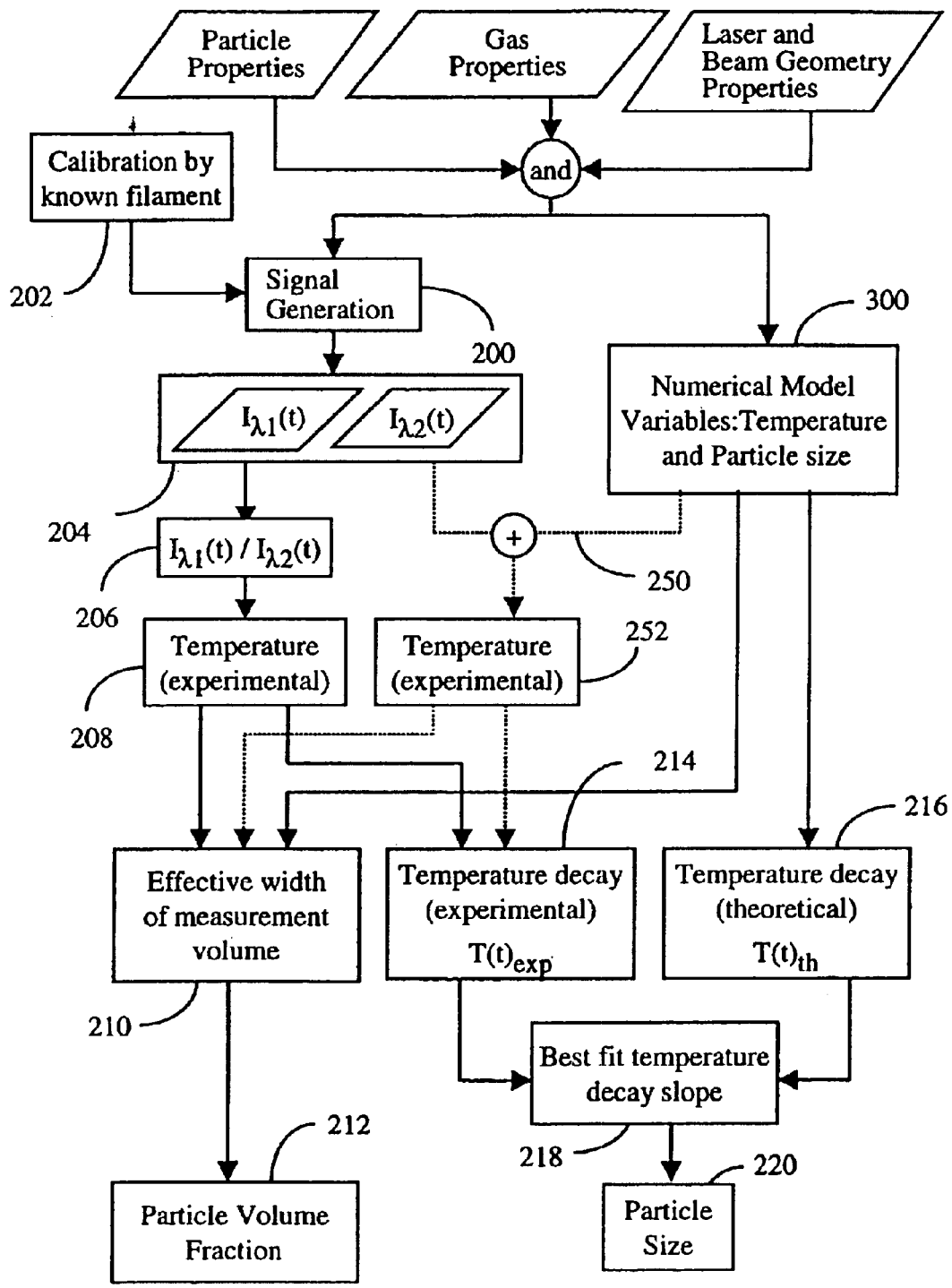
FIG. 6 is a flowchart illustrating the processes of the invention according to further embodiments. The processes are for determining particle volume fraction and particle size according to the arrangements in which a low fluence pulsed laser light beam and a non top hat fluence profile are used.

FIG. 6 shows another flowchart in accordance with other embodiments of the invention, in that a low fluence pulsed laser light beam is used in the arrangement in which the fluence profile is not "top hat" but is definable. The LII measurement may be made at one wavelength in one embodiment and two or more in other embodiments. Like the arrangement in FIG. 5, signal generation 200 involves properties of particle, gas and laser beam geometry. Calibration 202 can also be performed. LII signals are measured at one, two or more wavelengths at 204. In the embodiment in which LII signals are measured at two or more wavelengths, the ratio 206 of LII signals indicates the experimental particle temperature at 208. With the aid of the numerical modeling 300, a non top hat fluence profile is compensated to generate the effective width of the measurement volume at 210, which in turn produces the particle volume fraction at 212. Meanwhile, the experimental time dependent temperature decay curve 214 is compared with the theoretical time dependent temperature decay curve 216 produced by numerical modeling at 218 to produce the best fit, which determines the particle size at 220. FIG. 6 also shows in dotted lines 250 the embodiment in which LII is measured at one wavelength. In that embodiment, measured LII signal 204 is compensated by the numerical modeling 300 to generate the experimental temperature 252, which is used to generate the particle volume fraction and particle size as in the earlier embodiment with the help of the numerical modeling 300.

Figure 8:
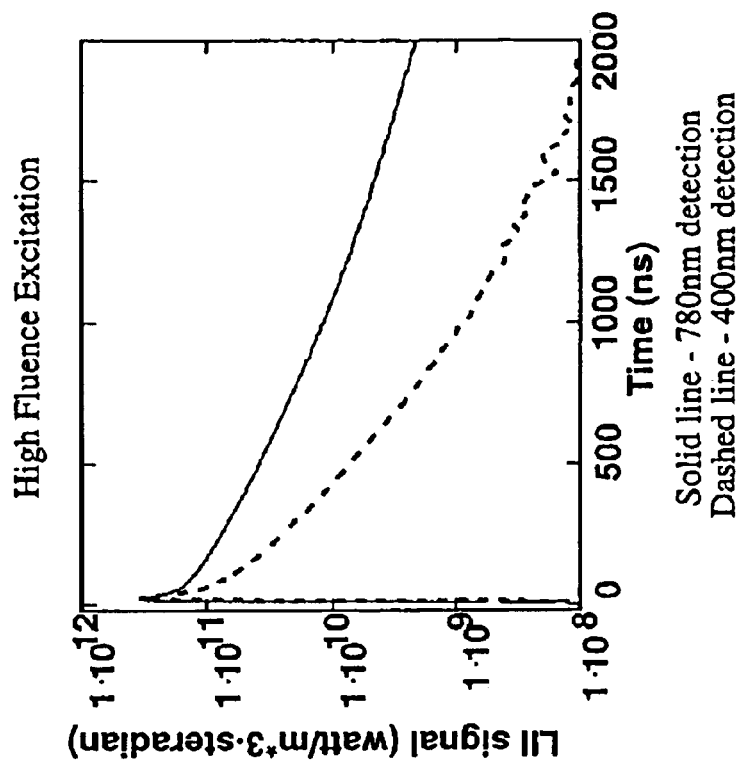
FIGS. 7–12 are graphs showing results of experiments using either a high fluence or a low fluence laser beam.
Figure 7:
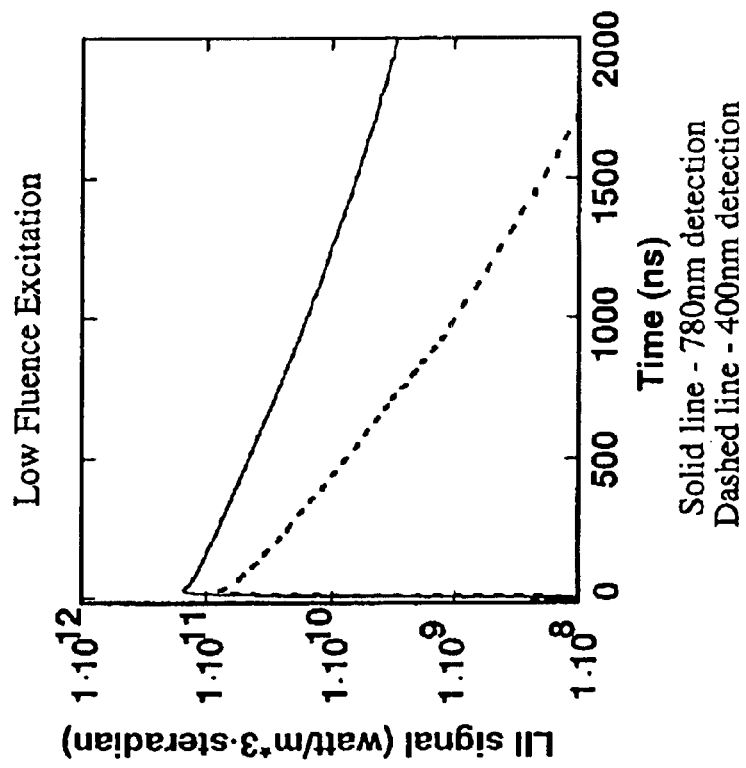
Figure 10:
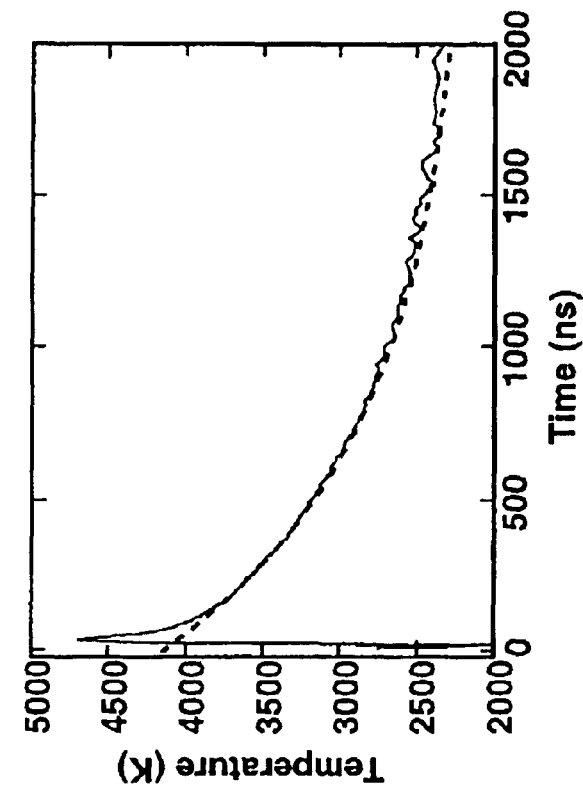
Figure 9:
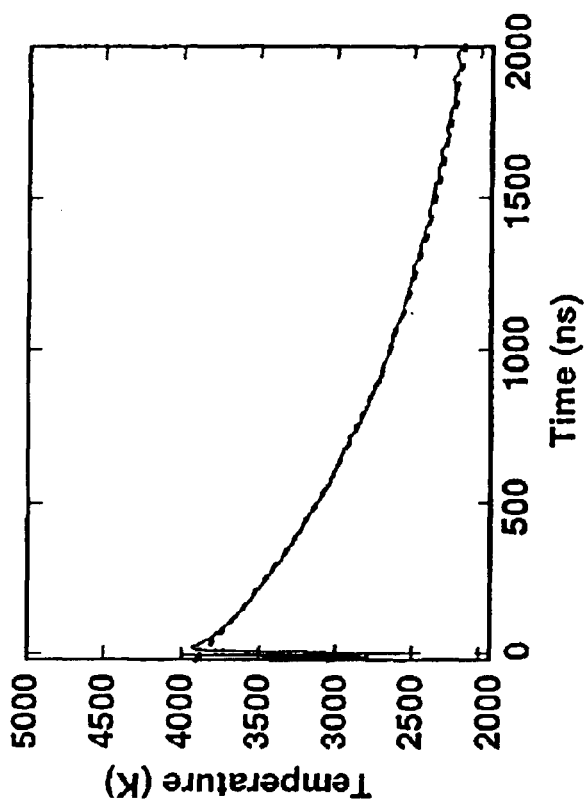

FIGS. 7–12 show graphs showing experimental results using either a low fluence or high fluence excitation. In particular, FIGS. 7 and 8 show absolute LII signals at 780 nm and 400 nm plotted in elapsed time beginning at the start of a laser pulse. Results of low fluence laser beam are in FIG. 7 and those of high fluence are in FIG. 8. The LII signals are in absolute intensity value in W/m$^3$ ·steradian and the time is in nanoseconds. In each figure, solid lines indicate 780 nm detection and dashed lines 400 nm detection. Immediately after a laser pulse, for both wavelengths, the intensities show a steady decrease with time for the low fluence laser beam, while for the high fluence laser beam, the intensities initially decrease rapidly, followed by a slower decrease. FIGS. 9 and 10 are graphs of soot surface temperature of the same experiment. FIG. 9 shows the results with low fluence laser beam, and FIG. 10 shows those with high fluence laser beam. In both figures, solid lines indicate temperatures as determined from experimental LII signals and dashed lines indicate best fit exponential decay. A better fit is obtained with low fluence laser beam in FIG. 9 than in the case of high fluence laser beam shown in FIG. 10. In the case of the high fluence laser beam, the particles are surrounded by vaporized or sublimated particulate material in addition to the ambient gas, which will affect the rate of heat conduction from the particle surface. As discussed earlier, the slope of the temperature decay is a measure of average particle size.

Figure 12:
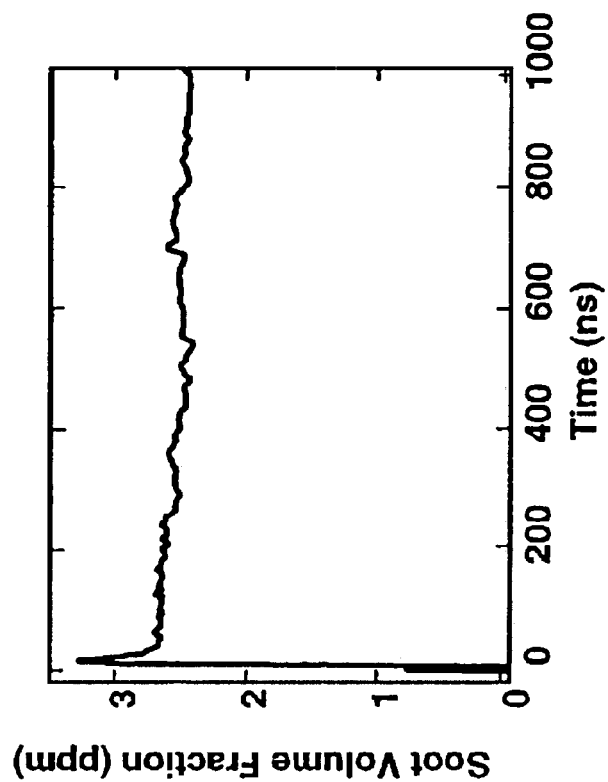
Figure 11:
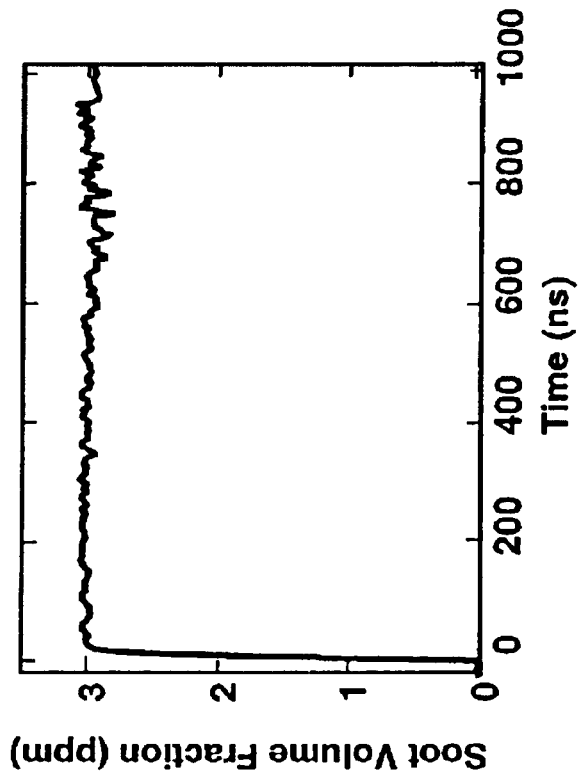

FIGS. 11 and 12 depict soot volume fraction (concentration) in ppm (parts per million) as determined by LII signals in experiments conducted with low fluence and high fluence laser beams respectively. The soot volume fraction in FIG. 1 indicates a stable value for a long period in the experiment with low fluence laser beam, suggesting that the measurements are accurate and very little evaporation is taking place. FIG. 12, on the other hand, shows an initially high value for concentration followed by a significant initial decrease and a fluctuation of values during a more gradual decrease. The decrease is believed to be the result of particle evaporation by the high fluence laser beam.

As seen from these graphs, it is quite evident that a low fluence laser beam produces better results. This is because excitation by the low fluence produces less evaporation of particles. Evaporation of the particles deleteriously interferes with heat conduction from the particles to the surrounding gas and causes unwanted reduction of the solid volume of the particles.

Of course, numerous other embodiments of the apparatus and method may be envisaged, without departing from the spirit and scope of the invention as defined in the appended claims.

What is claimed is:

1. A method of analyzing a plurality of submicron sized particles having a total solid volume $v_i$ within a volume of a surrounding medium, comprising steps of:
   a) heating the plurality of the particles to be analyzed with a laser light beam to a temperature such that a majority the submicron particles measurably incandesce, while ensuring that the temperature is sufficiently low such that no more than 5% of the solid volume $v_i$ is evaporated;
   b) measuring incandescence from the particles at one or more wavelengths; and,
   c) determining a characteristic of the particles in dependence upon the measured incandescence in step (b).

2. A method as defined in claim 1 wherein no more than 5% of the solid volume $v_i$ is evaporated during said heating and within a microsecond after heating.

3. A method as defined in claim 2, further comprising the step of calculating temperatures of the particles from the measured incandescence at a plurality of time intervals.

4. A method as defined in claim 2 wherein step (b) is performed by measuring incandescence from the particles at more than one wavelength.

5. A method as defined in claim 4 wherein step (b) is performed at more than one time interval.

6. A method as defined in claim 2, wherein the laser light beam is a pulsed laser light beam.

7. A method as defined in claim 2 wherein no more than 2% of the solid volume $v_i$ is evaporated during said heating and within a microsecond after heating.

8. The method as defined in claim 1, further comprising a step of:
processing the laser light beam to produce a substantially uniform laser fluence spatial profile at the volume of the surrounding medium.

9. The method as defined in claim 8, wherein the laser light beam is a pulsed laser light beam and, wherein the step of processing the pulsed laser light beam comprises steps of:
passing the pulsed laser light beam through an aperture to reduce the pulsed laser light beam to a region of substantially uniform fluence; and
relay imaging the aperture at the defined volume of the surrounding medium to produce a substantially constant laser fluence spatial profile.

10. The method according to claim 9, further comprising steps of:
calibrating the measured incandescence by a predetermined calibration factor.

11. The method according to claim 10, further comprising steps of:
measuring radiance from a light source of a known intensity at a predetermined temperature;
calculating theoretical radiance of the light source of a known intensity at the predetermined temperature; and
deriving the calibration factor from the measured and theoretical radiance.

12. The method as defined in claim 1 further comprising steps of:
measuring incandescence from the particles at two or more wavelengths;
generating digital signals indicative of the measured incandescence at the plurality of time intervals;
processing the digital signals to calculate the temperatures of the particles at the plurality of time intervals; and
analyzing the calculated temperatures to obtain a particle volume fraction.

13. The method as defined in claim 12 further comprising steps of:
generating a time dependent temperature decay characteristic; and
analyzing the time dependent temperature decay characteristic to obtain an average specific surface area of the particles or the average size of at least some of the particles.

14. The method as defined in claim 13 further comprising a steps of:
performing a numerical modeling of particles incandescing and dissipating energy to surrounding medium to generate theoretical time dependent temperature decay characteristics; and,
obtaining a best fit determination between the generated time dependent temperature decay characteristic and the theoretical time dependent temperature decay characteristics.

15. The method according to claim 1, further comprising steps of:
calibrating the measured incandescence by a predetermined calibration factor;
generating digital signals indicative of the measured incandescence at the plurality of time intervals;
processing the digital signals to calculate an average temperature of the particles at the plurality of time intervals;
performing a numerical modeling to generate an effective width of a sheet of the pulsed laser light beam at the defined volume of the surrounding medium; and
obtaining a particle volume fraction.

16. The method according to claim 15, further comprising steps of:
performing the numerical modeling to generate expected particle temperatures;
generating a time dependent temperature decay characteristic of particles; and
obtaining a best fit determination between the generated time dependent temperature decay characteristic and a theoretical time dependent temperature decay characteristic to obtain the average specific surface area of the particles or the average size of at least some of the particles.

17. The method as defined in claim 16, further comprising a step of:
performing a numerical modeling of particles incandescing and dissipating energy to the surrounding medium to generate the theoretical time dependent temperature decay characteristics.

18. A method as defined in claim 1, wherein the plurality of submicron sized particles having a total solid volume $v_i$ within a volume of of gas are soot particles and wherein at least 80% of the particles are heated with the laser light beam to a temperature such they measurably incandesce, and wherein 80% of the particles do not reach a temperature above 3900 K during said heating and detecting steps.

19. An apparatus for analyzing a plurality of submicron sized particles having a solid volume $v_i$ in a defined volume of gas by laser induced incandescence, comprising:
a laser for generating a pulsed laser light beam of a predetermined fluence;
an optical arrangement including an aperture in an optical path of the pulsed laser light beam for limiting the transmitted pulse to an area of substantially constant fluence;
imaging optics for forming a relay image of the aperture at a measurement location located within the defined volume of gas so that one or more particles in the defined volume of gas are heated by a constant fluence of the pulsed laser light beam and incandesce;
at least one photodetector for measuring incandescence from the particles at two or more wavelengths at a plurality of time intervals;
a signal processing unit for calculating temperatures of the particles at a plurality of time intervals;
a signal analyzer for analyzing a time dependent decaying of the calculated temperatures to obtain characteristics of the particles; and,
control means for controlling the fluence of the laser light beam such that a majority of the plurality of submicron particles measurably incandesce, while ensuring that the temperature is sufficiently low such that no more than 5% of the solid volume $v_i$ is evaporated.

20. The apparatus according to claim 19 wherein the aperture has parallel sides to adjust the defined volume such that the dimension of the defined volume along a detection axis is substantially constant over the region imaged by the photodetectors.

21. The apparatus according to claim 20 wherein the optical arrangement and imaging optics further comprise:
   one or more relay lenses disposed in the optical path with locations and focal lengths selected such that the desired pulsed laser light beam magnification and imaging of the aperture plane at the measurement location to minimize diffraction are simultaneously achieved; and,
   means disposed in the optical path to adjust the fluence of the pulsed laser light beam.

22. The apparatus according to claim 21 wherein the means disposed in the optical path further comprises:
   a half-wave plate and a polarizer.

23. The apparatus according to claim 22, wherein the signals processing unit and signal analyzer are digital modules and the apparatus further comprising:
   a digitizer for generating digital signals indicative of the measured incandescence at the plurality of time intervals.

24. The apparatus according to claim 23, further comprising:
   a computer which comprises the signals processing unit and signal analyzer, the computer further including software for conducting numerical modeling of particles incandescing and dissipating energy to the surrounding medium.

25. The apparatus according to claim 24, further comprising:
   an optical calibration arrangement for calibrating at least one photodetector with a light source of a known radiance.

26. The apparatus according to claim 24, further comprising:
   an optical calibration arrangement for calibrating photodetectors with a light source of a known radiance.

* * * * *